(12) United States Patent
Uchida et al.

(10) Patent No.: US 10,126,631 B2
(45) Date of Patent: Nov. 13, 2018

(54) TERAHERTZ WAVE GENERATOR AND TERAHERTZ WAVE MEASUREMENT METHOD

(71) Applicant: ARKRAY, Inc., Kyoto (JP)

(72) Inventors: Hirohisa Uchida, Kyoto (JP); Naoto Shichi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/146,892

(22) Filed: Jan. 3, 2014

(65) Prior Publication Data
US 2014/0191131 A1 Jul. 10, 2014

(30) Foreign Application Priority Data
Jan. 8, 2013 (JP) .................................. 2013-001153

(51) Int. Cl.
G02F 1/35 (2006.01)
G01N 21/3581 (2014.01)

(52) U.S. Cl.
CPC ....... *G02F 1/3544* (2013.01); *G01N 21/3581* (2013.01); *G02F 1/3534* (2013.01); *G02F 2001/3503* (2013.01); *G02F 2001/3507* (2013.01); *G02F 2203/13* (2013.01)

(58) Field of Classification Search
CPC ........... G01N 21/3581; G01N 21/3563; G01N 21/35; G01N 21/4738; G01N 21/55
USPC ...................................................... 250/341.8
See application file for complete search history.

(56) References Cited

U.S. PATENT DOCUMENTS

| | | | |
|---|---|---|---|
| 6,723,991 B1 * | 4/2004 | Sucha | G01J 11/00 250/330 |
| 6,828,558 B1 * | 12/2004 | Arnone et al. | 250/341.1 |
| 2003/0081221 A1 * | 5/2003 | Sanzari | 356/484 |
| 2006/0153255 A1 * | 7/2006 | Wada et al. | 372/32 |

(Continued)

FOREIGN PATENT DOCUMENTS

JP 2004-219967 A 8/2004
JP 2006-226910 A 8/2006

(Continued)

OTHER PUBLICATIONS

Ito et al. "Random Frequency Accessible Broad Tunable Terahertz-Wave Source Using Phase-Matched 4-Dimethylamino-N-methyl-4-Stilbazolium Tosylate Crystal" Japanese Journal of Applied Physics, vol. 46, No. 11, 2007, pp. 7321-7324, Aug. 20, 2007.*

(Continued)

*Primary Examiner* — David Porta
*Assistant Examiner* — Mamadou Faye
(74) *Attorney, Agent, or Firm* — Morgan, Lewis & Bockius LLP

(57) ABSTRACT

Excitation light of two wavelengths is incident to an optical crystal from a first face side, and a terahertz wave $THz_b$ is generated from a second face, and the excitation light that has passed through the optical crystal is reflected, made incident to the optical crystal from the second face side, and a terahertz wave $THz_a$ is generated from the first face. Terahertz waves with similar characteristics to each other are thereby generated reliably in plural directions.

11 Claims, 14 Drawing Sheets

(56) References Cited

U.S. PATENT DOCUMENTS

| | | | | |
|---|---|---|---|---|
| 2010/0072368 A1* | 3/2010 | Boegli | ............... | G01J 3/10 |
| | | | | 250/338.4 |
| 2010/0148070 A1* | 6/2010 | Ho | ............... | G01N 21/3581 |
| | | | | 250/341.8 |
| 2010/0157414 A1* | 6/2010 | Livingston | ............... | 359/332 |
| 2011/0103801 A1* | 5/2011 | Breunig | ............ | H04B 10/2575 |
| | | | | 398/118 |
| 2012/0193554 A1* | 8/2012 | Uchida | ............... | 250/504 R |

FOREIGN PATENT DOCUMENTS

| | | | |
|---|---|---|---|
| JP | 2008277959 A | * | 11/2008 |
| JP | 2009-276389 A | | 11/2009 |
| JP | 2010-204488 A | | 9/2010 |
| JP | 2012-177896 A | | 9/2012 |

OTHER PUBLICATIONS

Shibuya et al., "Terahertz-Wave Generation Using a 4-Dimethylamino-N-methyl-4-stilbazolium tosylate Crystal Under Intra-Cavity Conditions," Applied Physics Express, 1: pp. 42002-1 to 42002-3 (2008).

Suizu et al., "Prism-coupled Cherenkov phase-matched terahertz wave generation using a DAST crystal," Optics Express, 18: 3338-3344 (2010).

Office Action issued in corresponding Japanese Patent Application No. 2013-001153 dated Aug. 30, 2016.

\* cited by examiner

TERAHERTZ WAVE GENERATOR AND TERAHERTZ WAVE MEASUREMENT METHOD

CROSS-REFERENCE TO RELATED APPLICATION

This application is based upon and claims the benefit of priority of Japanese Patent Application No. 2013-1153, filed on Jan. 8, 2013 the entire contents of which are incorporated herein by reference.

TECHNICAL FIELD

The present invention relates to a terahertz wave generator and to a terahertz wave measurement method.

BACKGROUND ART

There is a proposal (see for example Japanese Patent Application Laid-Open (JP-A) No. 2004-219967) for a broad band terahertz wave generator that by adopting a cascade configuration, employing a common reflection mirror for a first oscillator and a second oscillator that oscillate with different wavelengths, as an optical parametric oscillator for 2-wavelength oscillation, implements stable 2-wavelength oscillation in which even when one wavelength is changed, there is no change imparted to the oscillation state of the other wavelength. A terahertz wave measurement apparatus is also proposed equipped with such a terahertz wave generator and a room temperature operating detector.

There is also a proposal (see for example JP-A No. 2009-276389) for a spectrometer in which: signal light and pump light from a pump light source are multiplexed by a nonpolarization beam splitter to generate multiplexed light, this is amplified by a fiber amplifier, and then the multiplexed light is divided in two to multiplexed light A and B by a polarization beam splitter, and the multiplexed light A and B are mixed by a polarization beam splitter so as to overlap in a GaP crystal at the phase matching angle which they form. Terahertz waves are thereby radiated in two directions, with a terahertz wave from the difference frequency mixing of the pump light in the multiplexed light B with the signal light in the multiplexed light A and a terahertz wave from the difference frequency mixing of the pump light in the multiplexed light A with the signal light in the multiplexed light B. One of the terahertz waves that are radiated in the two directions can thereby serve as reference light.

There is also a proposal for a terahertz wave generator capable of generating terahertz waves with different spectral characteristics using a single optical crystal (see, for example, JP-A No. 2012-177896). In the terahertz wave generator of JP-A No. 2012-177896, an optical crystal is configured by sticking together a DAST crystal and a DASC crystal such that their a axes are aligned. A terahertz wave caused by the DAST crystal is generated when excitation light is made incident to the DASC crystal side, and a terahertz wave caused by the DASC crystal is generated when excitation light is made incident to the DAST crystal side. Terahertz waves with different spectral characteristics can thereby be generated by a single optical crystal by switching the incident direction of excitation light incident to the optical crystal.

DISCLOSURE OF INVENTION

Technical Problem

However, in the terahertz wave generator described in JP-A No. 2004-219967, due to the terahertz wave being generated in one direction, light-splitting of the generated terahertz wave is required in some cases, for example, where terahertz waves are respectively illuminated onto a target substance and a reference substance. There is therefore an issue of a drop in power of the terahertz wave illuminated onto the target substance and the reference substance.

Moreover, although terahertz waves are generated in two directions in the terahertz wave generator of JP-A No. 2009-276389, there is still a need to illuminate the excitation light in a split state onto the crystal, and sometimes the output of the respective terahertz waves generated in two directions differs, due to stability characteristics of output of the excitation light that has been split into two. Moreover, there is also an issue of complicated mechanisms for splitting the excitation light and for detecting the terahertz waves generated in two directions.

Moreover, in the terahertz wave generator described in JP-A No. 2012-177896, the terahertz waves generated in two directions each have different characteristics from each other, and so there is an issue for example that it is not applicable to cases where it is desired to illuminate terahertz waves with similar characteristics to each other respectively onto a target substance and a reference substance.

The present invention addresses the above issues, and an object thereof is to provide a terahertz wave generator capable of reliable generation of terahertz waves with similar characteristics to each other in plural directions, and a terahertz wave measurement method capable of performing reliable terahertz wave measurement using such a terahertz wave generator.

Solution to Problem

In order to achieve the above object, a terahertz wave generator of the present invention includes: a nonlinear optical crystal that is disposed on an optical path of excitation light containing light with plural different wavelength components, and that generates a terahertz wave by difference frequency generation based on the incident excitation light; and plural detectors that detect each of terahertz waves generated in plural directions from the nonlinear optical crystal.

According to the terahertz wave generator of the present invention, the nonlinear optical crystal is disposed on the optical path of the excitation light containing light with plural different wavelength components. When the excitation light is incident to the nonlinear optical crystal, terahertz waves are generated from the nonlinear optical crystal by difference frequency generation based on the incident excitation light. Terahertz waves are thereby generated in plural directions from the nonlinear optical crystal disposed on a single optical path of the excitation light. The terahertz waves generated in plural directions from the nonlinear optical crystal are then respectively detected by plural detectors.

Since the terahertz waves are generated in plural directions from the nonlinear optical crystal disposed on the optical path of the excitation light, this accordingly enables plural terahertz waves with similar characteristics to be reliably generated.

In the terahertz wave generator of the present invention, configuration may be made such that the excitation light is made incident in a direction from a first face of the nonlinear optical crystal towards a second face on an opposite side from the first face, the excitation light that has passed through the nonlinear optical crystal is made incident in a direction from the second face towards the first face, and terahertz waves are respectively generated from the first face and the second face by collinear phase matching. This thereby enables terahertz waves with similar characteristics to each other to be generated respectively from the first face and the second face of the nonlinear optical crystal. Note that the first face and the second face may be flat faces or curved faces, and may be unprocessed faces obtained by a manufacturing method of the nonlinear optical crystal, or may be faces obtained by processing such as grinding, machining or cutting.

Moreover, the terahertz wave generator of the present invention may be configured including an excitation light generator that is equipped with a first mirror and a second mirror that together with the first mirror configures an oscillator, and that generates the excitation light. Moreover, the terahertz wave generator of the present invention may be configured further including a pair of off-axis parabolic mirrors that each include a pass-through portion through which excitation light passes and a reflection face that reflects incident terahertz waves, and that are each disposed so as to reflect the incident terahertz waves, wherein the nonlinear optical crystal is disposed between the pair of off-axis parabolic mirrors. Consequently, terahertz waves with similar characteristics to each other can be generated from the first face and the second face of the nonlinear optical crystal using such a simple configuration.

Moreover, the nonlinear optical crystal may have a shape with at least two flat faces. The two flat faces may oppose each other, and may be substantially parallel to each other.

Moreover, in the terahertz wave generator of the present invention, configuration may be made such that the nonlinear optical crystal has a shape with at least a first flat face and a second flat face on an opposite side from the first flat face, and terahertz waves are generated in plural directions by Cherenkov phase matching by making the excitation light incident from a side face of the nonlinear optical crystal. More specifically, terahertz waves are respectively generated from the first flat face and the second flat face of the nonlinear optical crystal. This thereby enables terahertz waves with similar characteristics to each other to be generated in plural directions from the nonlinear optical crystal.

Moreover, the terahertz wave generator of the present invention, may be configured to further include: an excitation light generator that is equipped with a first mirror and a second mirror that together with the first mirror configures an oscillator, and that generates the excitation light. This thereby enables, with such a simple configuration, terahertz waves with similar characteristics to each other to be generated from the first flat face and the second flat face of the nonlinear optical crystal.

Moreover, the terahertz wave generator of the present invention may be configured to further including a guide-wave body that is provided at at least one of the first flat face or the second flat face of the nonlinear optical crystal and that guides a terahertz wave generated from the nonlinear optical crystal in a direction according to a generation direction. The guide-wave body enables the terahertz waves generated by Cherenkov phase matching to be extracted to outside of the nonlinear optical crystal.

Moreover, the nonlinear optical crystal may be plate shaped.

Moreover, the terahertz wave generator of the present invention may be configured to further include a placement section for placing a sample on at least one optical path of a generated terahertz wave. This thereby enables a terahertz wave that has passed through a sample or been reflected by the sample to be detected when a sample is placed in the placement section, and enables a generated terahertz wave to be directly detected when a placement section is not provided or when a sample is not provided in the placement section.

Moreover, each of the plurality of detectors may be an imaging apparatus for capturing an image according to intensity of a generated terahertz wave. This thereby enables terahertz wave detection results to be imaged.

Moreover, a terahertz wave measurement method of the present invention includes, in the above terahertz wave generator: illuminating the excitation light onto the nonlinear optical crystal; illuminating at least one out of terahertz waves generated in plural directions from the nonlinear optical crystal onto a sample; and using the detectors to detect a terahertz wave that has passed through the sample or been reflected by the sample, or to directly detect a generated terahertz wave. This thereby enables reliable terahertz wave measurement to be performed using terahertz waves with similar characteristics to each other.

Moreover, the terahertz wave measurement method of the present invention may be configured such that the terahertz waves generated from the nonlinear optical crystal in the plural directions is illuminated onto at least one of a measurement sample or a reference sample. For example, one of the terahertz waves generated in plural directions from the nonlinear optical crystal may be illuminated onto a measurement sample, and another of the terahertz wave may be illuminated onto a reference sample. Moreover, each of the terahertz waves generated in plural directions from the nonlinear optical crystal may be illuminated onto different measurement samples or reference samples.

Advantageous Effects of Invention

As explained above, according to the terahertz wave generator of the present invention the advantageous effect is obtained of enabling terahertz waves with similar characteristics to each other to be reliably generated in plural directions, due to the terahertz waves being generated in plural directions from the nonlinear optical crystal disposed on the optical path of the excitation light. Moreover, according to the terahertz wave measurement method of the present invention, reliable terahertz wave measurement can be performed using the above terahertz wave generator.

DESCRIPTION OF EMBODIMENTS

Detailed explanation follows regarding an exemplary embodiment of a terahertz wave generator according to the present invention, with reference to the drawings.

Figure 1:
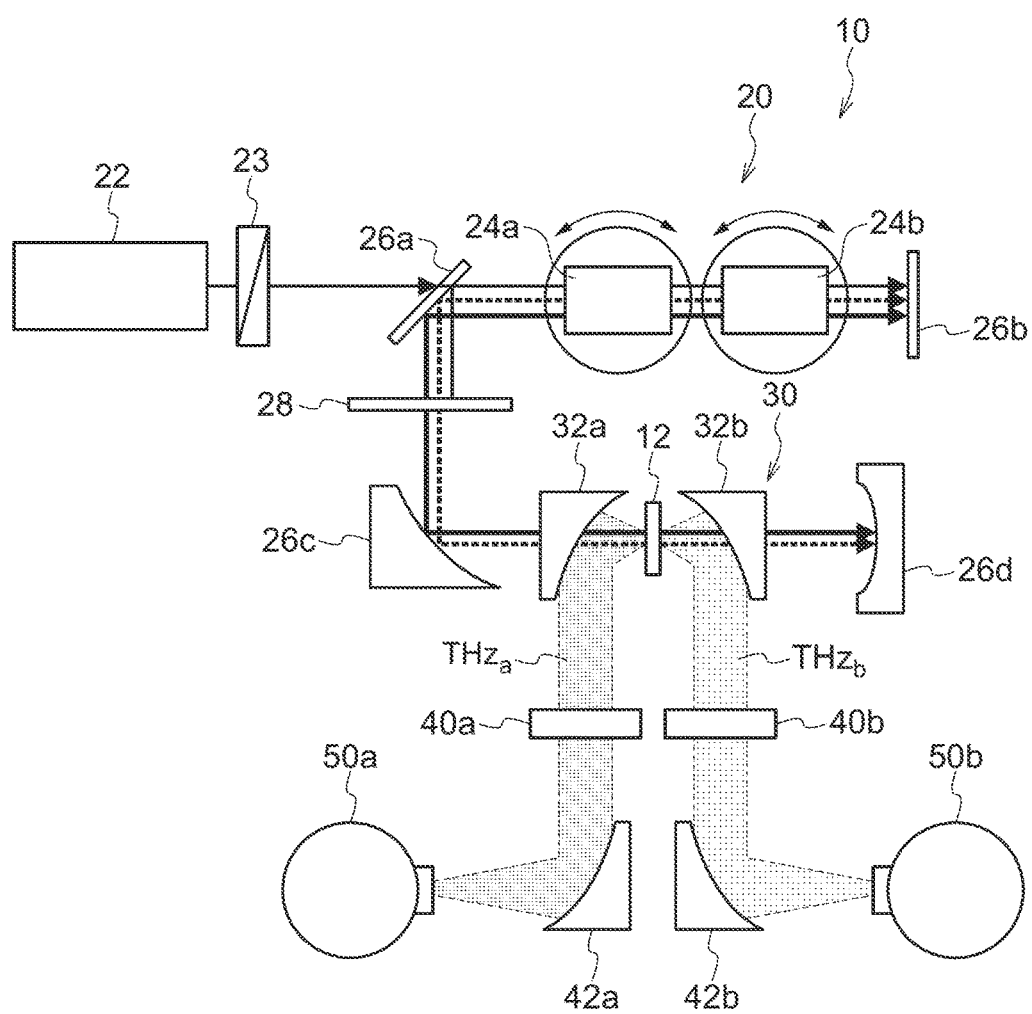
FIG. 1 is a schematic diagram illustrating a configuration of a terahertz wave generator according to a first exemplary embodiment.

As illustrated in FIG. 1, a terahertz wave generator 10 according to a first exemplary embodiment is configured including: a KTP parametric oscillator (KTP-OPO) 20 that generates excitation light of two different wavelengths; a terahertz wave generation section 30 that is disposed in the KTP-OPO 20; placement sections 40a, 40b provided for sample placement on the optical paths of each of the two terahertz waves generated by the terahertz wave generation section 30; parabolic mirrors 42a, 42b that guide the light of each of the terahertz waves; and detectors 50a, 50b that detect each of the guided terahertz waves.

The KTP-OPO 20 is configured including: an optical pump light source 22, a half-wavelength plate 23, two potassium titanium phosphate ($KTiPO_4$, KTP) crystals 24a, 24b; a mirror 26a, a mirror 26b, an off-axis parabolic mirror 26c, a concave mirror 26d, and an unwanted-light-cut filter 28.

The optical pump light source 22 is a light source that outputs pump light that acts as the source for generation of excitation light of two wavelengths in the KTP-OPO 20 and, for example, a YAG laser (wavelength: 532 nm, pulse width: 24 ns, recurrence frequency: 50 Hz) may be employed therefor. The mirror 26a, the two KTP crystals 24a, 24b and the mirror 26b are disposed in sequence along the extension of the optical path of the pump light.

The KTP crystals 24a, 24b are each mounted on a rotation stage, to enable independent adjustment of the incident angle of the pump light as incident to the respective crystals. The frequency of the excitation light generated from the KTP-OPO 20 can be changed by changing the incident angle of pump light onto the KTP crystals 24a, 24b.

A dichromatic mirror that allows the pump light (wavelength 532 nm) to pass through, and has a high reflectivity to light of wavelengths from 1300 nm to 1500 nm may be employed as the mirror 26a. The mirror 26a is disposed at an angle of 45° to the optical path of the pump light. A mirror with a high reflectivity to light of wavelengths from 1300 nm to 1500 nm may be employed as the mirror 26b. The mirror 26b is disposed perpendicularly to the optical path of the pump light. The unwanted-light-cut filter 28 and the off-axis parabolic mirror 26c are disposed in sequence along a direction perpendicular to the optical path of the pump light, that is one direction out of two branch directions produced by the mirror 26a.

The unwanted-light-cut filter 28 is a filter that removes wavelength components of the pump light (wavelength 532 nm). The unwanted-light-cut filter 28, prior to the excitation light being incident on an optical crystal 12, removes wavelength components of pump light remaining in the excitation light, such that excitation light is incident to the optical crystal 12 at high precision.

The off-axis parabolic mirror 26c has high reflectivity to light of wavelengths from 1300 nm to 1500 nm, and also converges the incident excitation light and reflects the incident excitation light in a direction perpendicular to the excitation light incident direction. The terahertz wave generation section 30 and the concave mirror 26d are disposed in sequence along the extension of the optical path of the excitation light reflected by the off-axis parabolic mirror 26c.

The terahertz wave generation section 30 is configured including a pair of off-axis parabolic mirrors with hole 32a, 32b and the optical crystal 12, disposed between the pair of off-axis parabolic mirrors with hole 32a, 32b.

The optical crystal 12 is a nonlinear optical crystal that generates, from the incident light (excitation light) of two different wavelengths, a terahertz wave of wavelength corresponding to the difference frequency between the two different wavelengths by difference frequency generation. The optical crystal 12 according to the first exemplary embodiment may be any nonlinear optical crystal that satisfies conditions of collinear phase matching may be employed therefor, such as for example 4-dimethyl amino -N-methyl-4-stilbazolium tosylate (DAST) crystals or 4-dimethyl amino -N-methyl-4-stilbazolium p-chlorobenzensulfonate (DASC) crystals.

Figure 2:
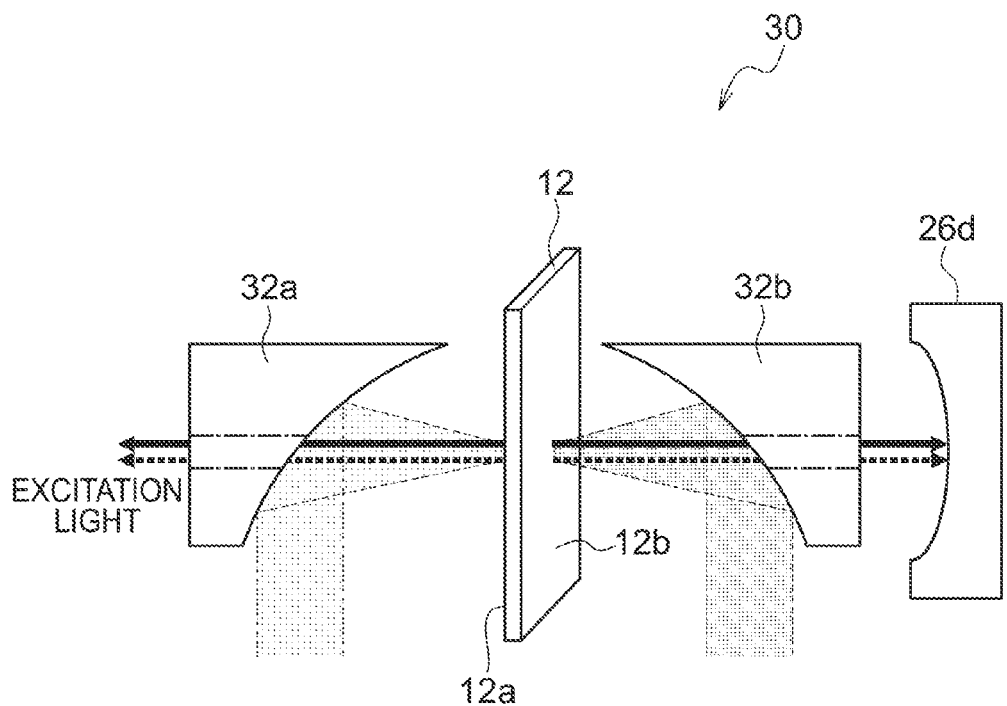
FIG. 2 is a schematic diagram illustrating a configuration of a terahertz wave generation section of the first exemplary embodiment.

The pair of off-axis parabolic mirrors with hole 32a, 32b are off-axis parabolic mirrors with a hole bored through the center (illustrated with single dot broken lines in FIG. 2, not illustrated in FIG. 1). The off-axis parabolic mirror with hole 32a and the off-axis parabolic mirror with hole 32b are disposed such that the excitation light passes through their holes, and such that their parabolic faces face each other. More specifically, as illustrated in FIG. 2, the off-axis parabolic mirror with hole 32a is disposed on a first flat face 12a side of the optical crystal 12, and the off-axis parabolic mirror with hole 32b is disposed on a second flat face 12b side of the optical crystal 12. The pair of off-axis parabolic mirrors with hole 32a, 32b are disposed such that the excitation light passes through their respective holes, and such that a terahertz wave $THz_a$ generated from the first flat face 12a and a terahertz wave $THz_b$ generated from the second flat face 12b are reflected in a perpendicular direction to the respective terahertz wave incident directions.

Note that when the optical crystal 12 satisfies conditions for collinear phase matching, the optical axis of the excitation light and the optical axis of the terahertz wave $THz_a$, and the optical axis of the excitation light and the optical axis of the terahertz wave $THz_b$ have a relationship of being in the same direction as each other. Therefore the off-axis parabolic mirror 26c, the concave mirror 26d, the pair of off-axis parabolic mirrors with hole 32a, 32b should be disposed along the optical path of the excitation light (the optical path of the terahertz wave that has a unidirectional relationship to the optical axis).

Figure 3:
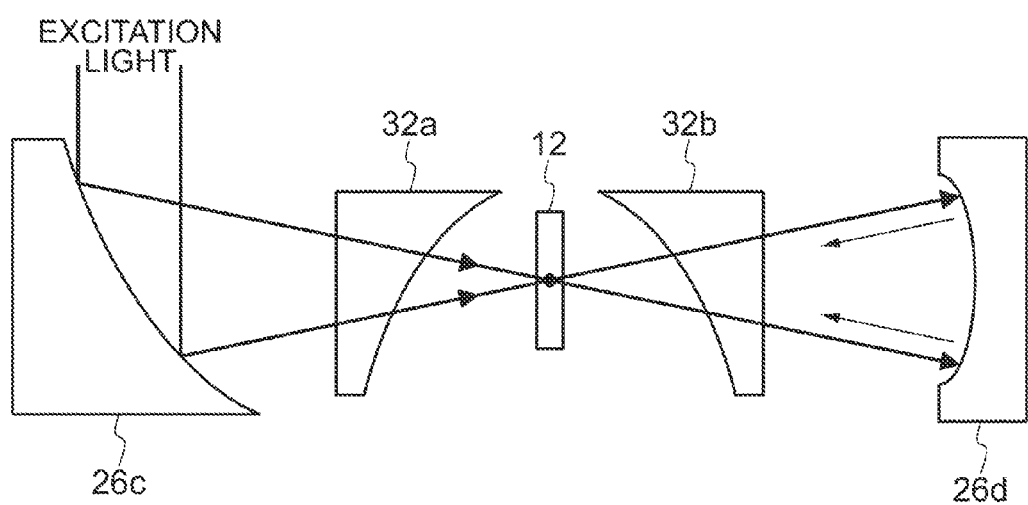
FIG. 3 is a schematic diagram to explain the curvature of a convex mirror.

A concave mirror with a high reflectivity to light of wavelengths from 1300 nm to 1500 nm may be employed as the concave mirror 26d. The concave mirror 26d is disposed so as to reflect the excitation light that has passed through the terahertz wave generation section 30, and to cause the excitation light to once again be incident on the terahertz wave generation section 30. The curvature of the concave mirror 26d is, as illustrated in FIG. 3, adjusted such that the focal point aligns with a point of the optical crystal 12 (marked by a dot in FIG. 3), and such that the reflected excitation light returns along the excitation light incident direction towards the concave mirror 26d.

The placement sections 40a, 40b are sample stages for placing measurement samples or reference samples. The placement section 40a is provided on the optical path of the terahertz wave $THz_a$ that has been generated from the first flat face 12a of the optical crystal 12 and reflected by the off-axis parabolic mirror with hole 32a. The placement section 40b is provided on the optical path of the terahertz wave $THz_b$ that has been generated from the second flat face 12b of the optical crystal 12 and reflected by the off-axis parabolic mirror with hole 32b.

The parabolic mirrors 42a, 42b reflect the terahertz waves $THz_a$, $THz_b$ that have passed through the placement sections 40a, 40b towards the direction where the detectors 50a, 50b are placed. Note that explanation is given here of a case in which terahertz waves that have passed through the placement sections 40a, 40b are detected, however configuration may be made such that the terahertz waves that have been reflected at the placement sections 40a, 40b are detected.

Explanation next follows regarding operation of a terahertz wave generator 10 according to the first exemplary embodiment.

First, when pump light is output from the optical pump light source 22, in the KTP-OPO 20, the pump light passes through the mirror 26a and is incident to the KTP crystals 24a, 24b, and excitation light of two different wavelengths (from 1300 to 1500 nm) is generated. The generated excitation light is reflected at the mirror 26b and the mirror 26a, wavelength components of remaining pump light are removed by the unwanted-light-cut filter 28, and the excitation light carries on in the direction towards the off-axis parabolic mirror 26c. The excitation light reflected at the off-axis parabolic mirror 26c is made incident to the terahertz wave generation section 30.

The excitation light passes through the hole of the off-axis parabolic mirror with hole 32a, and is incident to the optical crystal 12 from the first flat face 12a side. A terahertz wave $THz_b$ is then generated from the second flat face 12b side of the optical crystal 12. The generated terahertz wave $THz_b$ is reflected at the parabolic face of the off-axis parabolic mirror with hole 32b, however excitation light that has passed through the optical crystal 12 then passes through the hole of the off-axis parabolic mirror with hole 32b and is reflected at the concave mirror 26d.

The excitation light reflected at the concave mirror 26d passes once again through the hole of the off-axis parabolic mirror with hole 32b, and is incident to the optical crystal 12 from the second flat face 12b side. The terahertz wave $THz_a$ is then generated from the first flat face 12a side of the optical crystal 12. The generated terahertz wave $THz_a$ is reflected at the parabolic face of the off-axis parabolic mirror with hole 32a, the excitation light that has passed through the optical crystal 12 then passes through the hole of the off-axis parabolic mirror with hole 32a, is reflected by the off-axis parabolic mirror 26c and the mirror 26a, and returns in the direction towards the mirror 26b.

The terahertz wave $THz_a$ reflected at the off-axis parabolic mirror with hole 32a, and the terahertz wave $THz_b$ reflected at the off-axis parabolic mirror with hole 32b, accordingly pass through the respective placement sections 40a, 40b, and are reflected by the parabolic mirrors 42a, 42b so as to be incident to the detectors 50a, 50b.

Explanation next follows regarding a terahertz wave measurement method employing the terahertz wave generator 10 according to the first exemplary embodiment.

First, a Sample a is placed in the placement section 40a, and a Sample b is placed in the placement section 40b. Pump light is then output from the optical pump light source 22, excitation light of two different wavelengths is generated in the KTP-OPO 20, and is incident to the terahertz wave generation section 30. Consequently the terahertz wave $THz_a$ generated from the optical crystal 12 is illuminated onto the Sample a placed in the placement section 40a. However, the terahertz wave $THz_b$ generated from the optical crystal 12 is illuminated onto the Sample b placed in the placement section 40b.

Then at the detector 50a a measurement result of the Sample a (for example a terahertz wave spectrum) is acquired by detecting the terahertz wave that has passed through the placement section 40a. At the same time, at the detector 50b a measurement result of the Sample b is acquired by detecting the terahertz wave that has passed through the placement section 40b.

Note that the Sample a and the Sample b may each be employed as the measurement sample or as the reference sample. The combination of the Sample a and the Sample b may be employed as a measurement sample and a reference sample, as a measurement sample and a measurement sample, or as a reference sample and a reference sample. Configuration may be made such that a terahertz wave detected without disposing a sample in the placement sections 40a, 40b is acquired as a measurement result.

For example, a measurement sample is placed in one section out of the placement section 40a or the placement section 40b, and a reference sample is placed in the other of the placement section 40a or the placement section 40b. Then, using the terahertz wave spectrum of the reference sample detected by one section out of the detector 50a or the detector 50b, a measurement sample spectrum may be obtained at a single time of measurement by dividing a terahertz wave spectrum of a measurement substance detected by the other section out of the detector 50a or the detector 50b by the reference sample as a reference.

Explanation next follows regarding tests using the terahertz wave measurement method using the terahertz wave generator 10 according to the first exemplary embodiment.

In tests, a terahertz wave generator 10 is used that employs DAST crystals as the optical crystal 12. Samples employed are (1) PE (polyethylene 100%, reference sample), (2) $KClO_4$ (polyethylene 90%, $KClO_4$ 10%), and (3) Glu (polyethylene 90%, Glu 10%). The samples (2) and (3), are polyethylene pellets blended with $KClO_4$ and glucose (Glu) at a concentration that replaces 10% of the mass of the polyethylene. As measurement conditions a wavelength component $\lambda 1$ of the excitation light is set at 1350.5 nm, and a spectrum is obtained that is variably over a frequency range of 1.7 to 2.7 THz. Frequency resolution is 0.1 THz at 100 times of integration. Note that the measurement conditions may be set at any conditions that obtain a terahertz wave spectrum.

Figure 4:
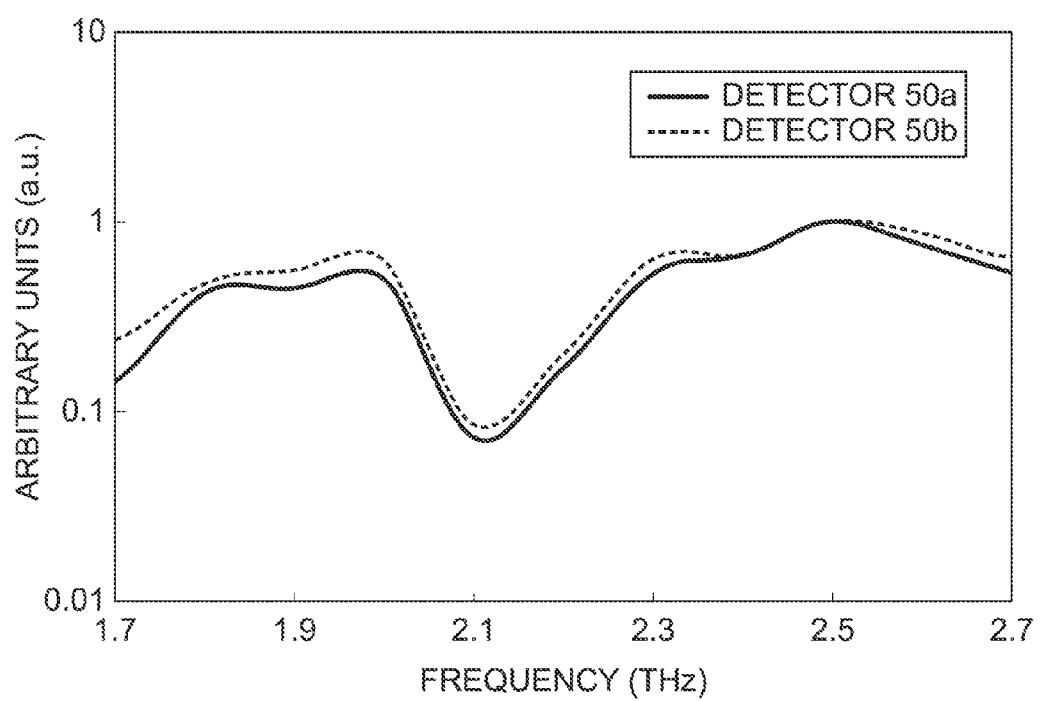
FIG. 4 is a graph illustrating simultaneously detected terahertz wave spectra.
Figure 5:
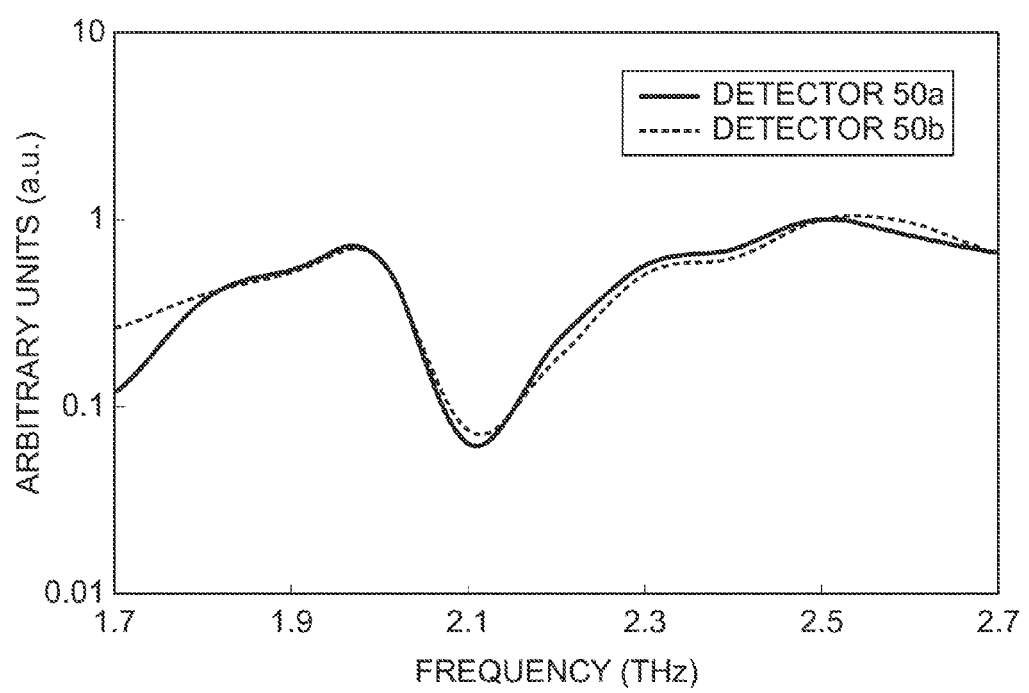
FIG. 5 is a graph illustrating simultaneously detected terahertz wave spectra of a reference sample.

FIG. 4 illustrates terahertz wave spectra from DAST crystals detected with the detectors 50a, 50b in a state in which a sample is not placed in either of the placement sections 40a, 40b. FIG. 5 illustrates terahertz wave spectra detected with the detectors 50a, 50b in a state in which a PE reference sample is placed in both the placement sections 40a, 40b. As illustrated in FIG. 4 and FIG. 5, terahertz wave spectra are obtained with similar shapes in both the detectors 50a, 50b. This indicates that the terahertz waves generated in the plural directions from the optical crystal placed one optical path of the excitation light have similar characteristics to each other. Namely, with the terahertz wave generator 10 according to the first exemplary embodiment, it is possible to illuminate terahertz waves with the same characteristics at the same time onto both the placement section 40a and the placement section 40b.

Figure 6:
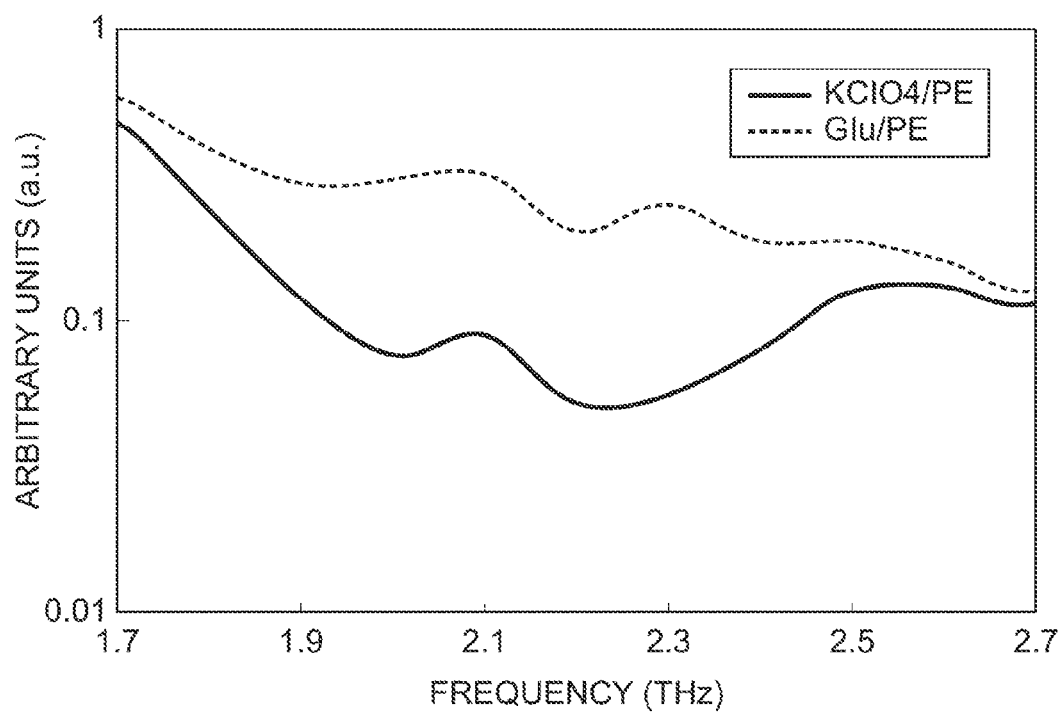
FIG. 6 is a graph illustrating terahertz wave spectra of measurement samples divided by simultaneously detected terahertz wave spectra of a reference sample.

Moreover, in the present tests, as the measurement conditions described above, the measurement sample KClO$_4$ is placed in one of the placement section 40a or the placement section 40b and the reference sample PE is placed in the other placement section 40a or the placement section 40b, and a spectrum (KClO$_4$/PE) is acquired of the KClO$_4$ terahertz wave spectrum detected by one of the detector 50a or the detector 50b, divided by the PE terahertz wave spectrum detected by the other of the detector 50a or the detector 50b as a reference. A spectrum (Glu/PE) is acquired in a similar manner using Glu as the measurement sample. As illustrated in FIG. 6, spectra can be acquired in the terahertz region for KClO$_4$ and glucose.

As explained above, according to the terahertz wave generator and the terahertz wave measurement method according to the first exemplary embodiment, terahertz waves can be generated respectively from a first flat face and a second flat face of the optical crystal by placing an optical crystal on one optical path of the excitation light, and causing the excitation light to be incident to the first flat face and to the second flat face of the optical crystal. Thus, for example, even when the output of the terahertz waves fluctuates due, for example, to wavering of the excitation light, or deterioration or damage to the optical crystal, since the terahertz wave generated from the first flat face and the terahertz wave generated from the second flat face are both influenced thereby, both the outputs of the terahertz waves fluctuate in a similar manner. Namely, according to the terahertz wave generator and the terahertz wave measurement method of the first exemplary embodiment, terahertz waves of similar characteristics can be stabilized and generated in plural directions. Moreover, since it is possible to illuminate the terahertz waves with similar characteristics onto plural samples at the same time, reliable terahertz wave measurement can be performed.

Figure 7:
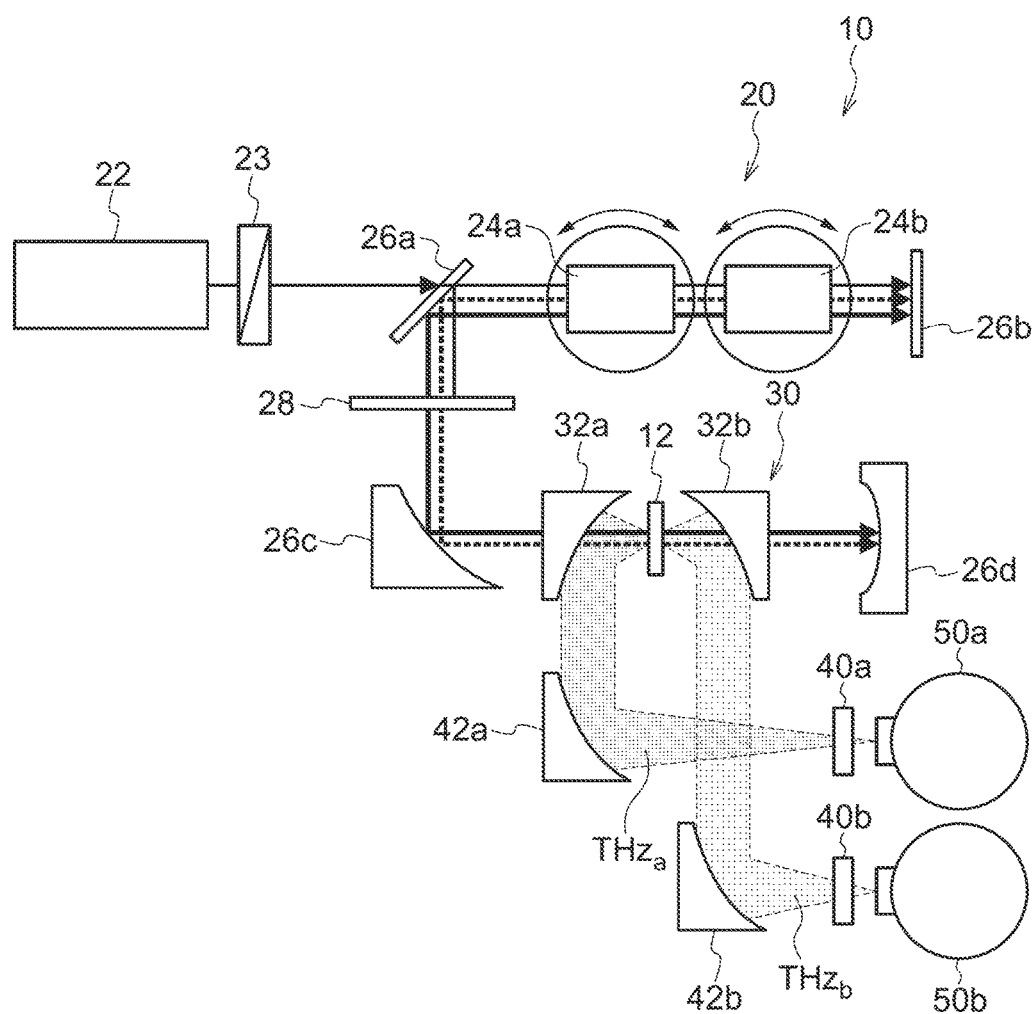
FIG. 7 is a schematic diagram illustrating a configuration of another terahertz wave generator according to the first exemplary embodiment.

Note that the placement of each configuration in the first exemplary embodiment is not limited to the example illustrated in FIG. 1. For example, as illustrated in FIG. 7, the parabolic mirrors 42a, 42b may be disposed between the pair of off-axis parabolic mirrors with hole 32a, 32b and the placement sections 40a, 40b so as to reflect terahertz waves towards detectors 50a, 50b that are placed in a row.

Figure 8:
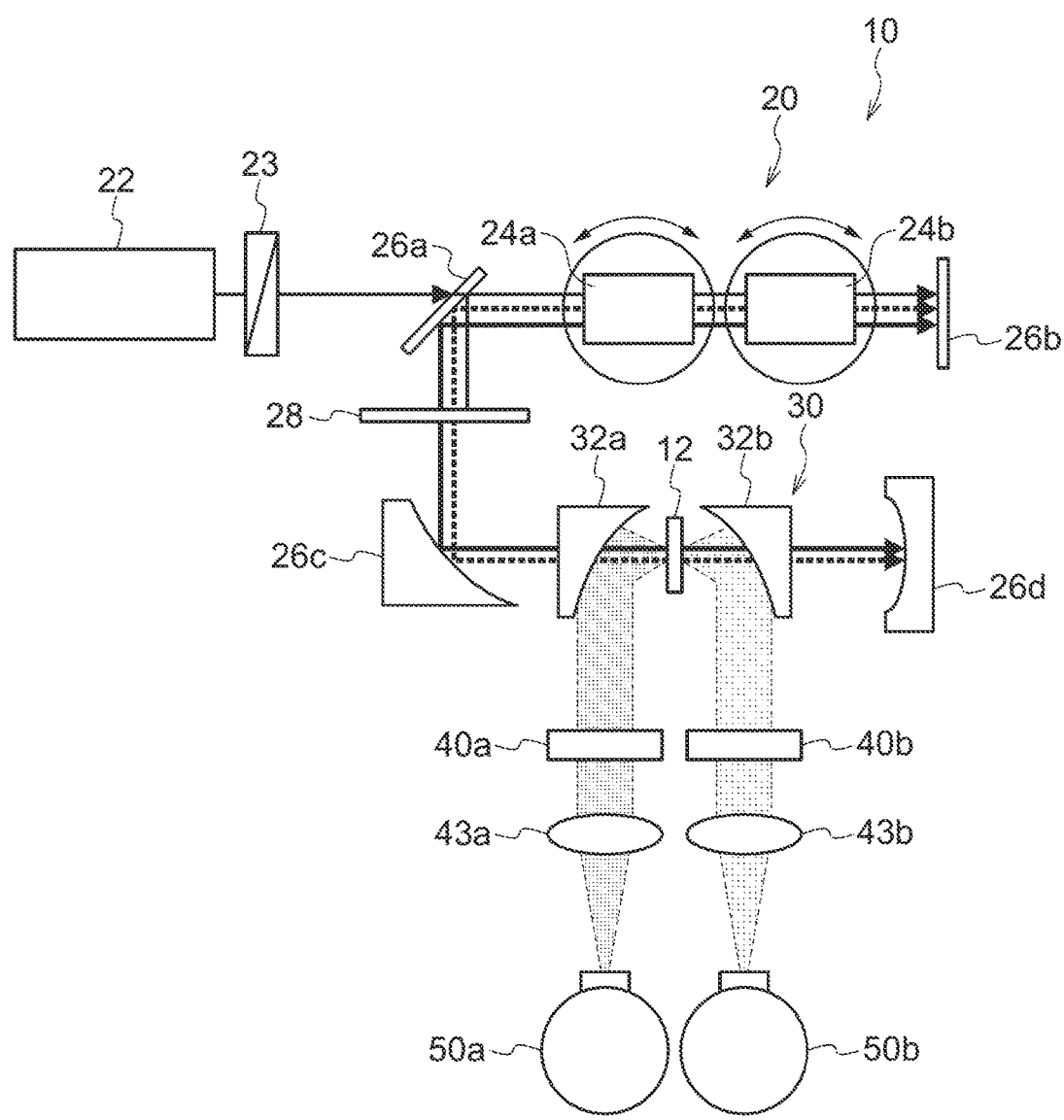
FIG. 8 is a schematic diagram illustrating a configuration of yet another terahertz wave generator according to the first exemplary embodiment.

Moreover, the parabolic mirrors 42a, 42b may be of any configuration that converges the terahertz waves and guides the terahertz waves towards the detectors 50a, 50b. For example, as illustrated in FIG. 8, terahertz wave converging lenses 43a, 43b may be employed in place of the parabolic mirrors 42a, 42b.

Figure 9:
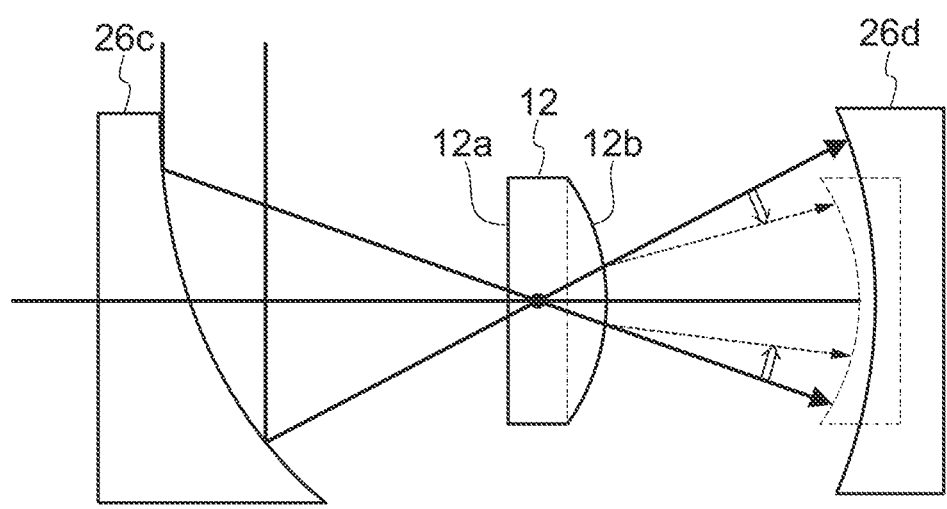
FIG. 9 is a schematic diagram to explain a relationship between a face of a nonlinear optical crystal and a curvature of a concave mirror.

Moreover, although explanation has been given in the first exemplary embodiment of a case such as illustrated in FIG. 2 in which an optical crystal is employed that has a first face and a second face that are flat faces, the first face and the second face are not limited to flat faces and curved faces may also be employed. For example, as illustrated in FIG. 9, an optical crystal 12 that has a convex second face may be employed. In such cases, the spread of the excitation light passing through the optical crystal 12 may be narrowed, as illustrated by the intermittent lines in FIG. 9. Adopting such an approach generates degrees of freedom for selecting the curvature of the concave mirror 26d. Moreover, when a face of the optical crystal is a concave face, although the amount of spreading of the excitation light passing through the optical crystal 12 is greater than with a convex face, it is possible to apply a greater curvature to the concave mirror 26d.

Explanation next follows regarding a second exemplary embodiment. Note that the same reference numerals are allocated to similar configurations in a terahertz wave generator according to the second exemplary embodiment to those of the terahertz wave generator 10 according to the first exemplary embodiment, and detailed explanation thereof is omitted.

Figure 10:
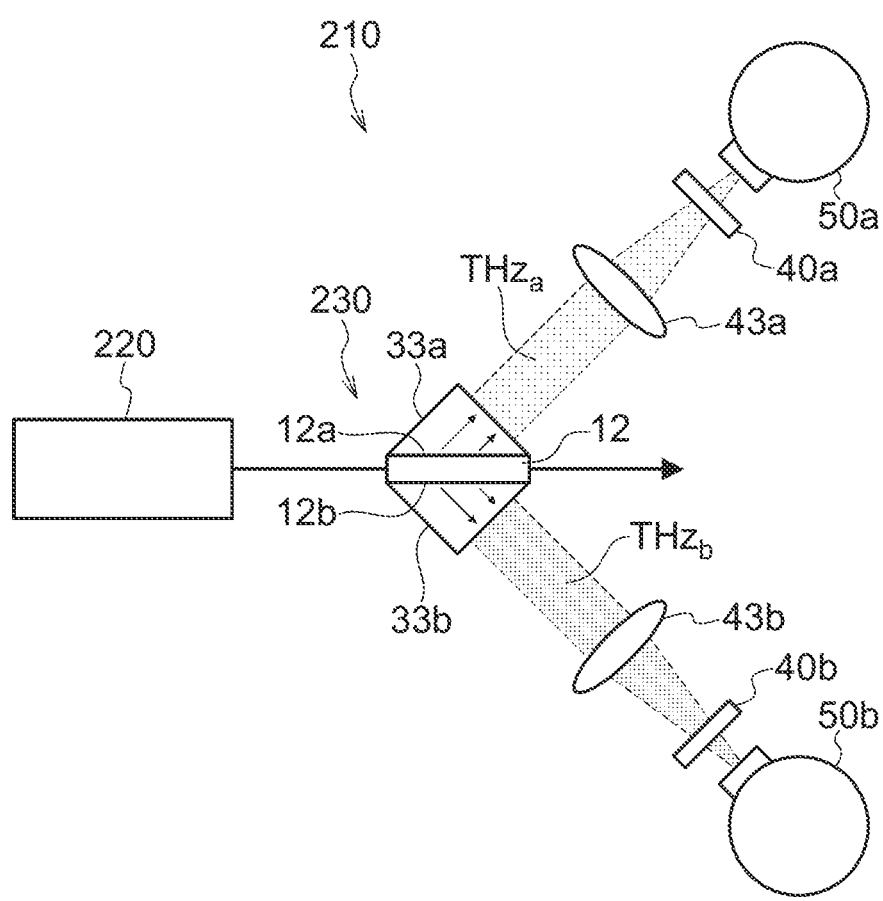
FIG. 10 is a schematic diagram illustrating a configuration of a terahertz wave generator according to a second exemplary embodiment.

As illustrated in FIG. 10, a terahertz wave generator 210 according to the second exemplary embodiment is configured including a femtosecond laser light source 220 that generates excitation light containing a plurality of wavelength components, a terahertz wave generation section 230, terahertz wave converging lenses 43a, 43b, placement sections 40a, 40b and detectors 50a, 50b.

The femtosecond laser light source 220 generates a femtosecond pulse laser (for example, central wavelength: 800 nm, pulse width: 80 fs, recurrence frequency 80 MHz) as excitation light.

The terahertz wave generation section 230 is configured including an optical crystal 12 and prisms 33a, 33b respectively provided on a first flat face 12a and a second flat face 12b of the optical crystal 12.

The optical crystal 12 may employ any nonlinear optical crystal that satisfies Cherenkov phase matching conditions, and similarly to in the first exemplary embodiment, a DAST crystal, a DASC crystal or the like may be employed therefor. The optical crystal 12 is formed in a plate shape with two flat faces (the first flat face 12a and the second flat face 12b), and is disposed such that the excitation light generated from the femtosecond laser light source 220 is incident onto a side face of the optical crystal 12 (a face other than the first flat face 12a and the second flat face 12b). A terahertz wave generated in the optical crystal 12 by Cherenkov phase matching propagates inside the optical crystal 12 respectively towards the first flat face 12a and the second flat face 12b at an angle according to the incident direction of the excitation light.

Figure 11:
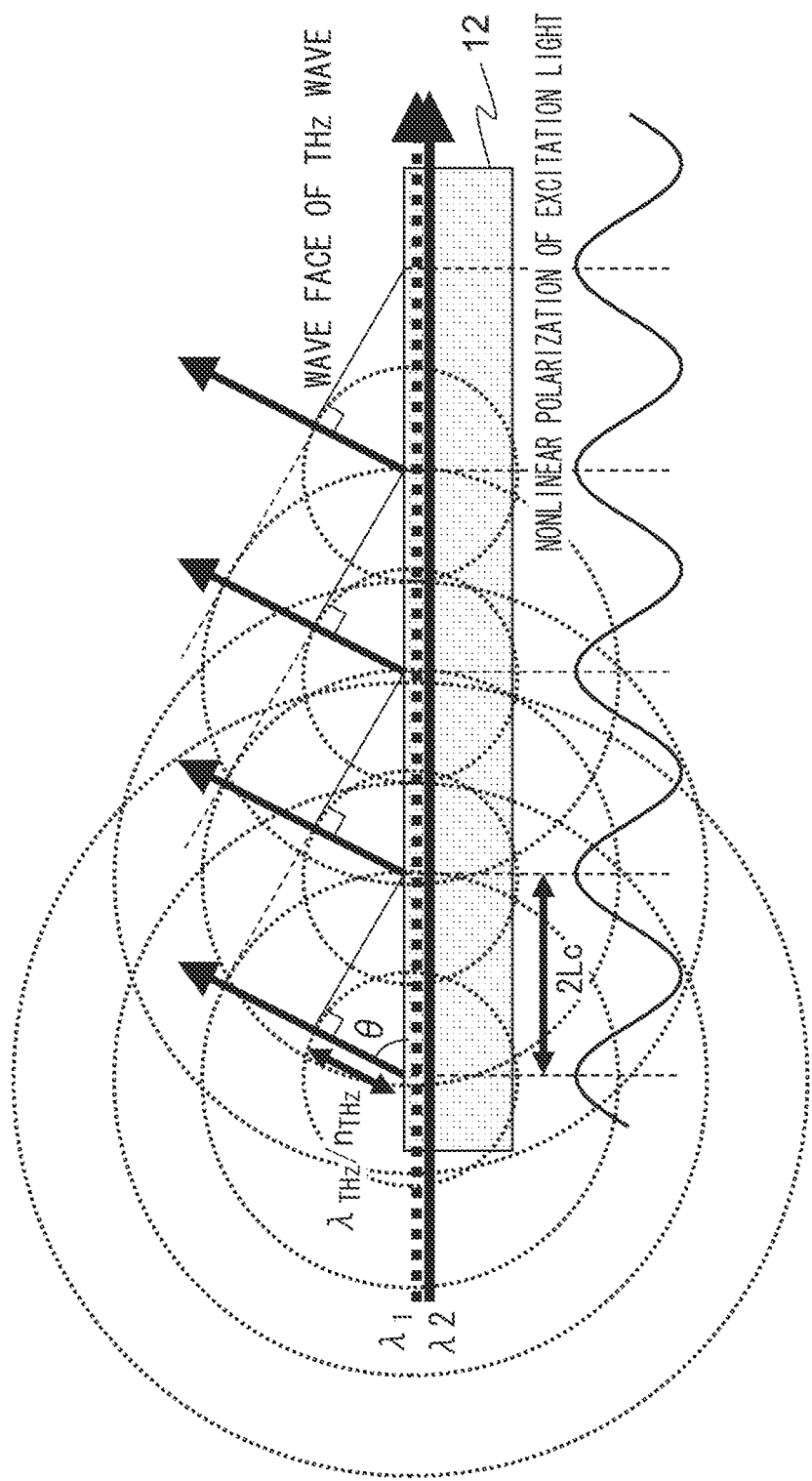
FIG. 11 is a schematic diagram to explain generation of terahertz waves under Cherenkov phase matching conditions.

More specifically, terahertz wave generation under Cherenkov phase matching conditions may be represented as illustrated in FIG. 11. When incident light (excitation light) of two different wavelengths is incident to the surface directly below the optical crystal 12, nonlinear polarization reaches maxima at 2 Lc, and a spherical wave is generated at each of these maxima. A terahertz wave is generated in the direction where the wave faces of the spherical waves overlap. The angle mentioned above according to the incident direction of the excitation light is indicated by the angle θ in FIG. 11, and the angle θ may be expressed by the following Equation (1).

$$\cos\theta = \frac{\lambda_{THz}/n_{THz}}{2Lc} = \frac{\lambda_{THz}/n_{THz}}{\lambda_1\lambda_2/(n_1\lambda_2 - n_2\lambda_1)} \quad (1)$$

wherein Lc is the coherence length, $\lambda_1$ is the wavelength of the incident light (excitation light) of one of the two different wavelengths, $n_1$ is the refractive index to $\lambda_1$ of the optical crystal 12, $\lambda_2$ is the wavelength of the incident light (excitation light) of the other of the two different wavelengths, $n_2$ is the refractive index to $\lambda_2$ of the optical crystal 12, $\lambda_{THz}$ is the wavelength of the terahertz wave generated by difference frequency generation from the incident light of two different wavelengths, and $n_{THz}$ is the refractive index of the optical crystal 12 to the terahertz wave generated by difference frequency generation from the incident light of two different wavelengths. Moreover, in the following θ is referred to as the radiation angle. Note that the radiation angle θ is an angle expressed with respect to the excitation light incident direction, and the radiation angle when the excitation light incident direction is from left to right as illustrated in FIG. 11 is denoted θ, and the radiation angle when the excitation light incident direction is in the opposite direction (from the right to the left in FIG. 11) is denoted −θ.

The prisms 33a, 33b extract the terahertz waves that have propagated inside the optical crystal 12 as far as the external boundary, to outside the optical crystal 12. Silicon prisms may, for example, be employed as the prisms 33a, 33b.

The converging lens 43a, the placement section 40a, and the detector 50a are disposed in sequence along the extension of the optical path of the terahertz wave $THz_a$ extracted from the first flat face 12a of the optical crystal 12 by the prism 33a. The converging lens 43b, the placement section 40b, and the detector 50b are disposed in sequence along the extension of the optical path of the terahertz wave $THz_b$ extracted from the second flat face 12b of the optical crystal 12 by the prism 33b.

Note that when the optical crystal 12 satisfies the conditions for Cherenkov phase matching, a terahertz wave is generated with the radiation angle θ of Equation (1) illustrated in FIG. 11, and extracted in a direction according to the refractive index of the prisms 33a, 33b. Consequently, the detectors 50a, 50b may be disposed on the optical path of the terahertz wave in a direction according to radiation angle θ and the refractive index of the prisms 33a, 33b.

Explanation next follows regarding operation of the terahertz wave generator 210 according to the second exemplary embodiment.

Excitation light is generated from the femtosecond laser light source 220, is incident to the side face of the optical crystal 12. The terahertz waves $THz_a$ and $THz_b$ then propagate within the optical crystal 12 respectively along the first flat face 12a direction and the second flat face 12b direction, are extracted by the prisms 33a, 33b, and are guided towards the direction of the converging lenses 43a, 43b. The terahertz waves $THz_a$, $THz_b$ that have been respectively converged by the converging lenses 43a, 43b pass through the placement sections 40a, 40b, and are incident onto the detectors 50a, 50b.

Note that the terahertz wave generator 210 according to the second exemplary embodiment may be employed to implement the above terahertz wave measurement method, similarly to in the first exemplary embodiment.

As explained above, according to the terahertz wave generator of the second exemplary embodiment, the optical crystal is placed on one optical path of the excitation light, and respective terahertz waves can be generated from the first flat face and the second flat face of an optical crystal by making excitation light incident from the side face of the optical crystal. Therefore, similarly to in the first exemplary embodiment, terahertz waves with similar characteristics to each other can be generated reliably in plural directions at the same time. Moreover, since the terahertz waves with similar characteristics to each other can be illuminated onto plural samples at the same time, this enables reliable terahertz wave measurement to be performed, similarly to in the first exemplary embodiment.

Explanation next follows regarding a third exemplary embodiment. Note that configuration in the terahertz wave generator according to the third exemplary embodiment similar to that of the terahertz wave generator 10 according to the first exemplary embodiment or the terahertz wave generator 210 according to the second exemplary embodiment is allocated the same reference numerals and detailed explanation is omitted thereof.

Figure 12:
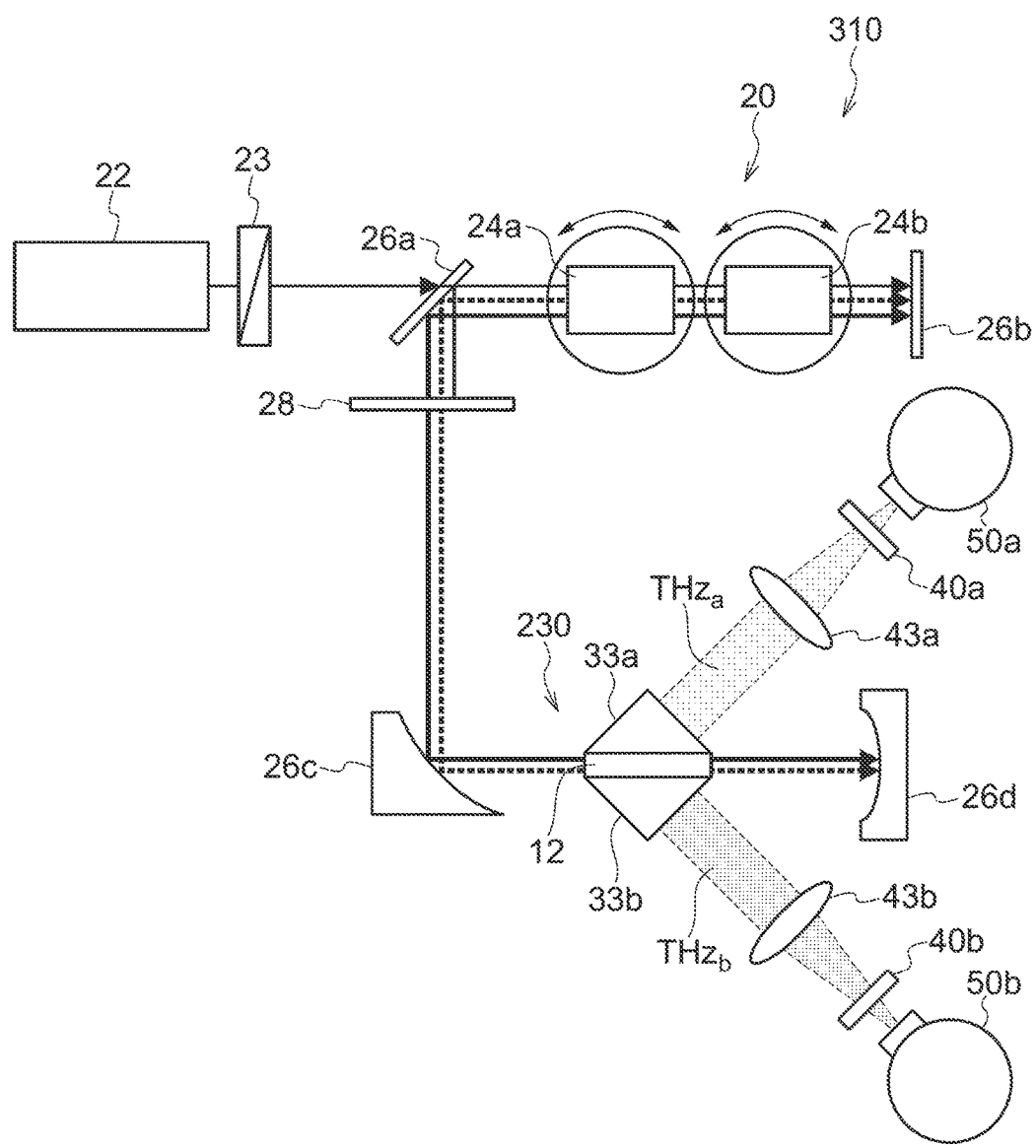
FIG. 12 is a schematic diagram illustrating a configuration of a terahertz wave generator according to a third exemplary embodiment.

As illustrated in FIG. 12, a terahertz wave generator 310 according to the third exemplary embodiment is configured including a KTP-OPO 20, a terahertz wave generation section 230, converging lenses 43a, 43b, placement sections 40a, 40b and detectors 50a, 50b.

The KTP-OPO 20 is, similarly to in the first exemplary embodiment, configured including an optical pump light source 22, a half-wavelength plate 23, two KTP crystals 24a, 24b, a mirror 26a, a mirror 26b, an off-axis parabolic mirror 26c, a concave mirror 26d and a unwanted-light-cut filter 28.

The terahertz wave generation section 230 is, similarly to in the second exemplary embodiment, configured by an optical crystal 12 and prisms 33a, 33b. Each configuration of the terahertz wave generation section 230 is disposed such that the excitation light reflected at the off-axis parabolic mirror 26c is incident to the side face of the optical crystal 12, and the excitation light reflected at the concave mirror 26d is incident to the side face on the other side of the optical crystal 12.

Moreover, similarly to in the second exemplary embodiment, the converging lens 43a, placement section 40a and the detector 50a are disposed in sequence along the extension of the optical path of the terahertz wave $THz_a$ extracted from the first flat face 12a of the optical crystal 12 by the prism 33a. The converging lens 43b, the placement section 40b and the detector 50b are disposed in sequence along the optical path extension of the terahertz wave $THz_b$ extracted from the second flat face 12b of the optical crystal 12 by the prism 33b.

Note that, similarly to in the second exemplary embodiment, the detectors 50a, 50b may be disposed on the optical path of the terahertz waves that arise in directions according to the radiation angle θ and the refractive index of the prisms 33a, 33b.

Operation of the terahertz wave generator 310 according to the third exemplary embodiment is similar to that in the first exemplary embodiment up to when the excitation light is incident to the terahertz wave generation section 230, and is similar to in the second exemplary embodiment from that point onwards, and so detailed explanation thereof is omitted.

Moreover, the terahertz wave generator 310 according to the third exemplary embodiment may also be employed to implement the terahertz wave measurement method described above similarly to in the first exemplary embodiment.

Figure 13:
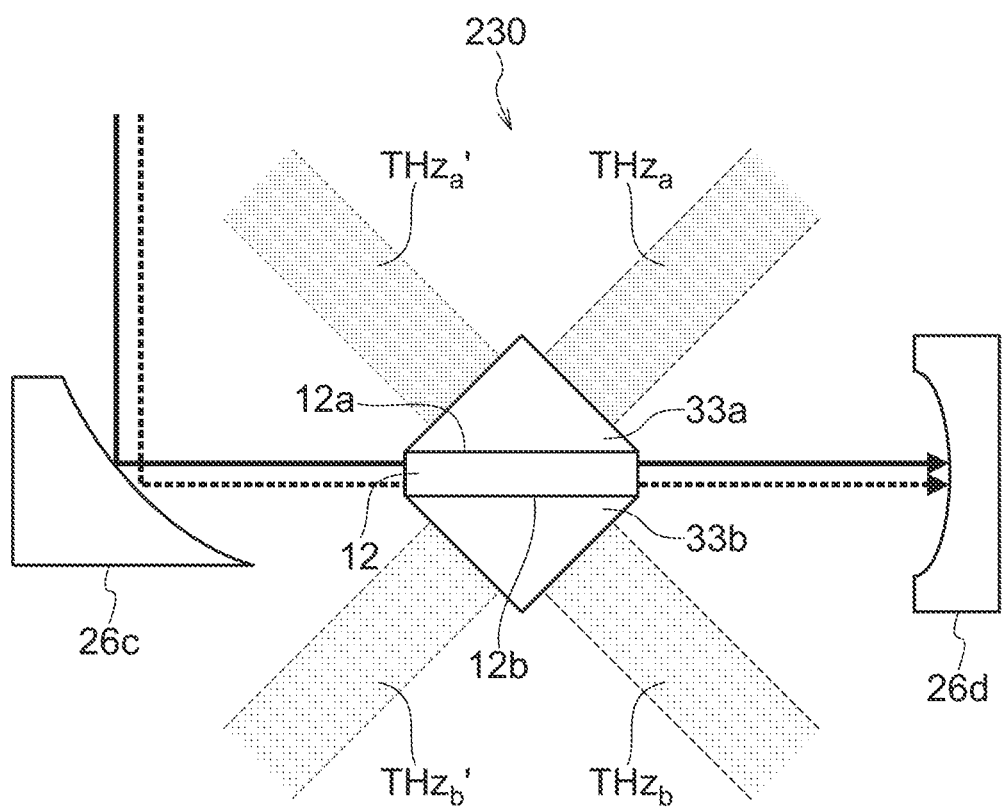
FIG. 13 is a schematic configuration diagram illustrating a configuration of a terahertz wave generation section according to the third exemplary embodiment.

Note that each element of the configuration of the third exemplary embodiment is not limited to the example illustrated in FIG. 12. When, as with the third exemplary embodiment, the terahertz wave generation section 230 for generating terahertz waves by Cherenkov phase matching is disposed within an oscillator, terahertz waves can be generated in four directions, as illustrated in FIG. 13. Specifically, when excitation light reflected at the off-axis parabolic mirror 26c is incident to the optical crystal 12 (when the excitation light progression direction is from the left to the right in FIG. 13), similarly to in the case of FIG. 12, the terahertz wave $THz_a$ is generated from the first flat face 12a of the optical crystal 12 and the terahertz wave $THz_b$ is generated from the second flat face 12b. Moreover, when the excitation light reflected at the concave mirror 26d is incident to the optical crystal 12 (when the excitation light progression direction is from the right to the left in FIG. 13), a terahertz wave $THz_a'$ is generated from the first flat face 12a of the optical crystal 12, and a terahertz wave $THz_b'$ is generated from the second flat face 12b. Since all these terahertz waves have similar characteristics to each other, terahertz wave measurement may be performed using a given two or more terahertz waves from out of these four terahertz waves. For example, the terahertz wave $THz_a$ and the terahertz wave $THz_a'$ may be employed, or the terahertz wave $THz_b$ and the terahertz wave $THz_b'$ may be employed. In such cases one of the prisms 33a, 33b may be omitted.

Figure 14:
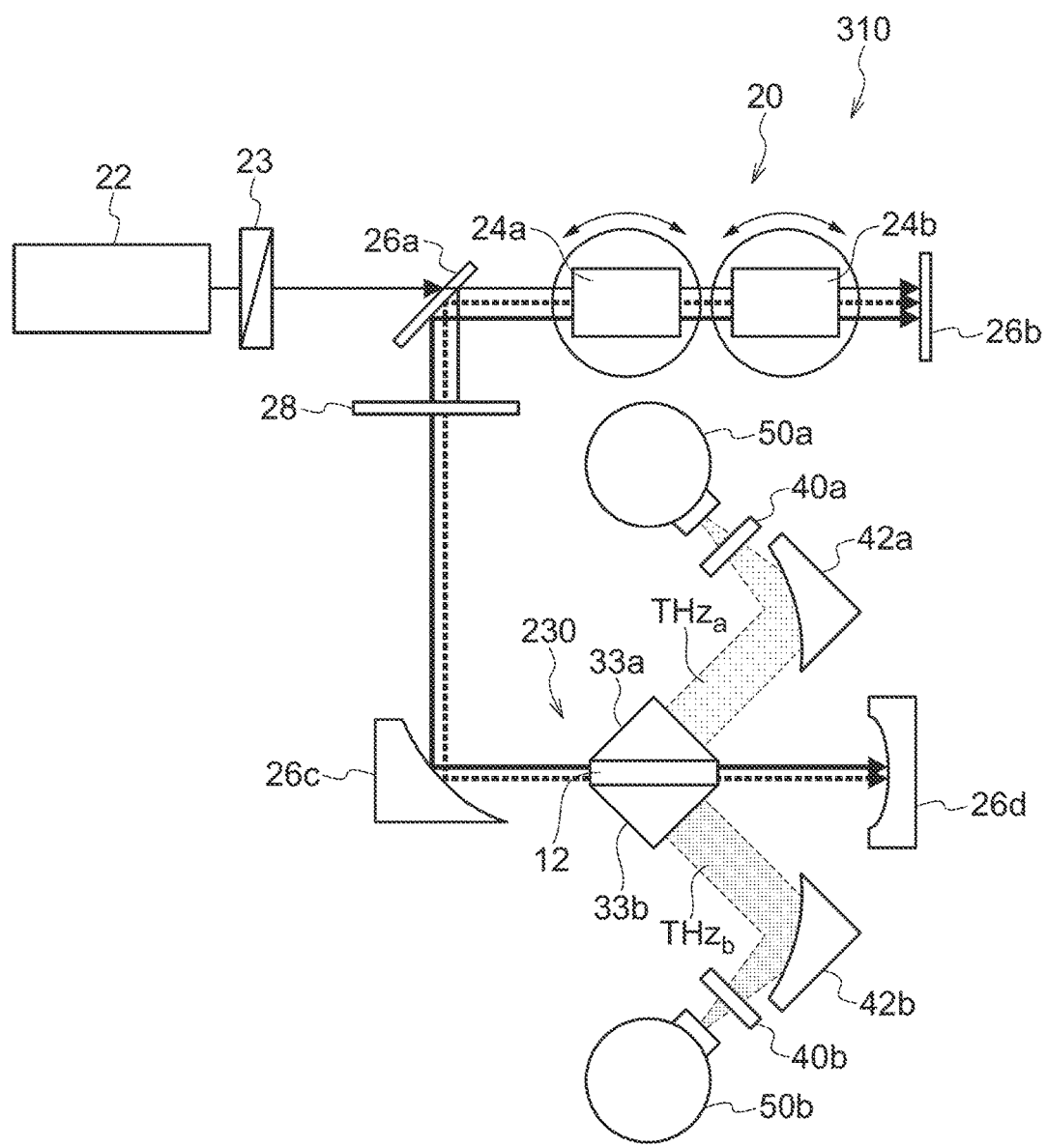
FIG. 14 is a schematic diagram illustrating another configuration of a terahertz wave generator according to the third exemplary embodiment.

Moreover, as illustrated in FIG. 14, parabolic mirrors 42a, 42b may be employed in place of the converging lenses 43a, 43b. In such cases, the parabolic mirrors 42a, 42b may be disposed on the optical path of the terahertz wave arising in the direction according to the radiation angle θ and the refractive index of the prisms 33a, 33b.

Moreover, explanation has been given in the first to the third exemplary embodiments described above of cases in which detectors are employed to detect the terahertz waves, however as detectors, for example, an imaging apparatus may be employed to capture an image according to the intensity of the terahertz waves. As an imaging apparatus, a terahertz camera, an infrared camera, a far infrared camera, a milliwave camera or the like may be employed that has sensitivity to terahertz band light. Moreover, an image according to the intensity of terahertz waves may be imaged by changing the pixel values (for example the contrast, color or brightness) of each of the pixels according to the relative intensity of the terahertz wave captured as light by a light capture section corresponding to each of the pixels.

The invention claimed is:

1. A terahertz wave generator comprising:
   a nonlinear optical crystal comprising a single crystal disposed in an optical path of excitation light of a plurality of different wavelength components, and configured to generate terahertz waves having similar characteristics from a first face and a second face of the single nonlinear optical crystal at the same time by difference frequency generation based on incident excitation light, the second face being on an opposite side from the first face;
   a plurality of placement sections comprising a first placement section provided for a reference sample placement and a second placement section provided for a measurement sample placement;
   a waveguide section configured to guide a first terahertz wave so as to be illuminated onto the first placement section without splitting, and a second terahertz wave so as to be illuminated at the same time onto the second placement section among terahertz waves generated from the nonlinear optical crystal without splitting and having similar characteristics; and
   a plurality of detectors configured to detect each terahertz wave that has passed through a respective placement section or has been reflected by a respective placement section,
   wherein a measurement result is obtained from each terahertz wave detected by a plurality of detectors at the same time, and
   wherein the terahertz waves are respectively generated from the first face and the second face by collinear phase matching by entry of the excitation light into the nonlinear optical crystal from the first face towards the second face of the nonlinear optical crystal, and by passage of the excitation light through the nonlinear optical crystal from the second face towards the first face of the nonlinear optical crystal.

2. The terahertz wave generator of claim 1, further comprising:
   an excitation light generator equipped with a first mirror and a second mirror that together with the first mirror forms an oscillator, where the excitation light generator is configured to generate the excitation light.

3. The terahertz wave generator of claim 1, further comprising:
   a pair of off-axis parabolic mirrors, with each mirror comprising a pass-through portion through which the excitation light passes and a reflection face that reflects incident terahertz waves, and that are each disposed so as to reflect the incident terahertz waves,
   wherein the nonlinear optical crystal is disposed between the pair of off-axis parabolic mirrors.

4. The terahertz wave generator of claim 1, wherein the nonlinear optical crystal has a shape with at least two flat faces.

5. The terahertz wave generator of claim 1, wherein the first face is flat and the second face is flat, and the terahertz waves are generated by Cherenkov phase matching when the excitation light is incident from the nonlinear optical crystal.

6. The terahertz wave generator of claim 5, further comprising:
   an excitation light generator equipped with a first mirror and a second mirror that together with the first mirror form an oscillator, and where the excitation light generator to generate the excitation light.

7. The terahertz wave generator of claim 5, further comprising a guide-wave body provided at one of the first flat face and/or the second flat face of the nonlinear optical crystal and configured to guide the terahertz wave generated from the nonlinear optical crystal in a direction according to a generation direction.

8. The terahertz wave generator of claim 1, wherein the nonlinear optical crystal is plate shaped.

9. The terahertz wave generator of claim 1, wherein each of the plurality of detectors is an imaging apparatus configured to capture an image according to intensity of a generated terahertz wave.

10. The terahertz wave generator of claim 1, wherein one of the terahertz waves generated from the nonlinear optical crystal in the plurality of directions is illuminated onto the measurement sample, and another of the terahertz waves is illuminated onto the reference sample.

11. The terahertz wave generator of claim 1, wherein each of the terahertz waves generated from the nonlinear optical crystal in the plurality of directions is illuminated onto different measurement samples or reference samples.

* * * * *